United States Patent [19]

Spira et al.

[11] Patent Number: 5,972,885
[45] Date of Patent: *Oct. 26, 1999

[54] METHOD FOR TREATMENT OF HEMOPHILIA BY EXTRAVASCULAR ADMINISTRATION OF FACTOR VIII DELETION DERIVATIVES

[75] Inventors: Jack Spira, Stockholm; Lars Widlund, Spånga; Thomas Österberg, Stockholm, all of Sweden

[73] Assignee: Pharmacia & Upjohn Aktiebolag, Stockholm, Sweden

[*] Notice: This patent issued on a continued prosecution application filed under 37 CFR 1.53(d), and is subject to the twenty year patent term provisions of 35 U.S.C. 154(a)(2).

[21] Appl. No.: 08/564,161

[22] PCT Filed: Mar. 31, 1994

[86] PCT No.: PCT/SE94/00297

§ 371 Date: Dec. 21, 1995

§ 102(e) Date: Dec. 21, 1995

[87] PCT Pub. No.: WO95/01804

PCT Pub. Date: Jan. 19, 1995

[30] Foreign Application Priority Data

Jul. 5, 1993 [SE] Sweden ................................. 9302308

[51] Int. Cl.$^6$ .......................... A61K 38/00; A61K 35/14; A01N 37/18
[52] U.S. Cl. .................................. 514/12; 514/2; 530/383
[58] Field of Search ........................... 514/12, 2; 530/383

[56] References Cited

U.S. PATENT DOCUMENTS

| | | | |
|---|---|---|---|
| 4,027,013 | 5/1977 | Bick et al. | 424/101 |
| 4,348,384 | 9/1982 | Horikoshi et al. | 424/101 |
| 4,746,508 | 5/1988 | Carey et al. | 424/88 |
| 4,868,112 | 9/1989 | Toole, Jr. | 435/68 |
| 4,904,584 | 2/1990 | Shaw | 435/69.4 |
| 5,112,950 | 5/1992 | Meulien et al. | 530/383 |
| 5,171,844 | 12/1992 | Van Oooyen et al. | 530/383 |
| 5,204,323 | 4/1993 | Findlay et al. | 514/2 |
| 5,563,045 | 10/1996 | Pittman et al. | 435/69.6 |
| 5,576,194 | 11/1996 | Chan | 435/69.6 |
| 5,585,112 | 12/1996 | Unger et al. | 424/450 |
| 5,587,310 | 12/1996 | Kane et al. | 435/240.2 |

FOREIGN PATENT DOCUMENTS

| | | |
|---|---|---|
| B-74868/87 | of 1987 | Australia . |
| 609829 | of 1988 | Australia . |
| 0 104 356 A1 | of 1984 | European Pat. Off. . |
| 0160457 | 11/1985 | European Pat. Off. . |
| 0 253 455 A1 | of 1988 | European Pat. Off. . |
| WO 91/09122 | of 1991 | WIPO . |
| 92/16557 | 10/1992 | WIPO . |
| WO 93/24137 | of 1993 | WIPO . |
| WO 94/26286 | of 1994 | WIPO . |

OTHER PUBLICATIONS

Graham–Pool et al. (1966) Ineffectiveness of intramuscularly injected Factor VIII concentrate in two hemophilic patients. New England Journal of Medicine 275 (10): 547–548, Sep. 1966.

Johnson et al. (1971) Clinical investigation of intermediate– and high–purity antihaemophilic factor (Factor VIII) concentrates. British Journal of Hematology 21: 21–41, Jan. 1971.

Liles et al. (1995) Lack of absorption of Factor VIII from extravascular sites: Key for future gene therapy of Hemophilia A. Blood 86 (Suppl. 1): 1001a, Jan. 1995.

Wood et al. (1984) Expression of active human factor VIII from recombinant DNA clones, Nature 312: 330–337, Nov. 22, 1984.

Mosby's Complete Drug Reference (1997) Physicians GenRx, pp. II–144 and II–145, Jan. 1997.

Pool et al., Ineffectiveness of Intramuscularly Injected Factor VIII Concentrate in Two Hemophilic Patients, Medical Intelligence, vol. 275, No. 10 (1966), pp. 547–548.

Gervasi et al., Decrease of Bleeding Time by a Peptide Fraction from Bovine Factor VIII in Laboratory Animals, Arzneim–Forsch./Drug Res., vol. 38, No. 9 (1988), pp. 1268–1270.

Wan et al., CMC of Polysorbates, Journal of Pharmaceutical Sciences, vol. 63, No. 1 (1974), pp. 136–137.

Anderson et al., Isolation and characterization of human factor VIII: Molecular forms in commercial factor VIII concentrate, cryoprecipitate, and plasma, Proc. Natl. Acad. Sci., Medical Sciences, vol. 83 (1986), pp. 2979–2983.

Burke et al., The Functional Domains of Coagulation Factor VIII:C*, The Journal of Biological Chemistry, vol. 261, No. 27 (1986), pp. 12574–12578.

Eaton et al., Construction and Characterization of an Active Factor VIII Variant Lacking the Central One–Third of the Molecule, The American Chemical Society, Biochemistry, vol. 25, No. 26 (1986), pp. 8343–8347.

Toole et al., A Large Region (≈95 KDa) of Human Factor VIII is Dispensable for in vitro Procoagulant Activity, Proc. Natl. Acad. Sci., vol. 83 (1986), pp. 5939–5942.

Primary Examiner—Bradley L. Sisson
Assistant Examiner—Einar Stole
Attorney, Agent, or Firm—Pollock, Vande Sande & Amernick

[57] ABSTRACT

A pharmaceutical formulation for subcutaneous, intramuscular or intradermal administration comprising recombinant coagulation factor VIII and use thereof for manufacture of a medicament for treating haemophilia is provided. The formulation comprises a highly purified recombinant coagulation factor VIII in a concentration of at least 1000 IU/ml, which gives surprisingly high levels of active factor VIII in the blood stream after subcutaneous, intramuscular or intradermal administration. The formulation is intended for treatment of haemophilia by subcutaneous, intramuscular or intradermal administration. The recombinant factor VIII is preferably a deletion derivative thereof, which can be used for the manufacture of a medicament for subcutaneous administration.

18 Claims, No Drawings

METHOD FOR TREATMENT OF HEMOPHILIA BY EXTRAVASCULAR ADMINISTRATION OF FACTOR VIII DELETION DERIVATIVES

This application claims the benefit of Swedish Application No. 9302308-3, filed on Jul. 5, 1993, and PCT/SE94/00297, filed Mar. 31, 1994.

The present invention relates to a pharmaceutical formulation for subcutaneous, intramuscular or intradermal administration comprising recombinant coagulation factor VIII and use thereof for manufacture of a medicament for treating haemophilia. The formulation comprises a highly purified recombinant coagulation factor VIII in a concentration of at least 1000 IU/ml, which gives surprisingly high levels of active factor VIII in the blood stream after subcutaneous, intramuscular or intradermal administration. The formulation is intended for treatment of haemophilia by subcutaneous, intramuscular or intradermal administration. The recombinant factor VIII is preferably a deletion derivative thereof, which can be used for the manufacture of a medicament for subcutaneous administration.

BACKGROUND OF THE INVENTION

Haemophilia is an inherited disease which has been known for centuries but it is only within the last three decades that it has been possible to differentiate between the various forms; haemophilia A, haemophilia B and haemophilia C. Haemophilia A is the most frequent form. It affects only males with an incidence of one or two individuals per 10 000 live-born males. The disease is caused by strongly decreased level or absence of biologically active coagulation factor VIII (antihaemophilic factor), which is a protein normally present in plasma. The clinical manifestation of haemophilia A is a strong bleeding tendency and before treatment with factor VIII concentrates was introduced, the mean age of those patients was less than 20 years. Concentrates of factor VIII obtained from plasma have been available for about three decades. This has improved the situation for treatment of haemophilia patients considerably and given them possibility to live a normal life.

Therapeutic factor VIII concentrates have until now been prepared by fractionation of plasma. However, there are now methods available for production of factor VIII in cell culture using recombinant DNA techniques as reported in e.g. J Gitschier et al. Nature 312, p.330–37, 1984 and EP-A-160 457.

Factor VIII concentrates derived from human plasma contain several fragmented fully active factor VIII forms (Andersson et al, Proc. Natl. Acad. Sci. USA, Vol 83, p. 2979–83, May 1986). The smallest active form has a molecular mass of 170 kDa and consists of two chains of 90 kDa and 80 kDa held together by a metal ion bridge. Reference is here made to EP-A-197 901. Kabi Pharmacia has developed a recombinant factor VIII product which corresponds to the 170 kDa plasma factor VIII form in therapeutic factor VIII concentrates. The truncated recombinant factor VIII molecule is termed r-VIII SQ and is produced by Chinese Hamster Ovary (CHO) cells in a cell culture process in serum-free medium.

The structure and biochemistry of recombinant factor VIII products in general have been described by Kaufman in Tibtech, Vol 9, 1991 and Hematology, 63, p. 155–65, 1991. The structure and biochemistry of r-VIII SQ have been described in WO-A-91/09122.

Large proteins are normally given intravenously so the medicament directly available in the blood stream. It would however be advantageous if a medicament could be given subcutaneously, intramuscularly or intradermally as these administration forms are much easier to handle for the patient. Especially if the medicament must be taken regularly during the whole life and treatment is to start early, already when the patient is a child. However, a medicament with a very large and labile molecule, such as coagulations factor VIII of 170 to 300 kDa, have normally a very low bioaviability if given subcutaneously, intramuscularly or intradermally, since the uptake is not enough and degradation is severe. To our knowledge, the only coagulation factor protein which has been administered by subcutaneous injection is factor IX (90 kDa).

All presently available factor VIII preparations on the market are made as a formulation for intravenous administration and are stabilised with human serum albumin.

DESCRIPTION OF THE INVENTION

To our great surprise we have found that factor VIII, which is a very sensitive protein, can be given subcutaneously and, in contrast to all earlier experience we obtain an acceptable absorption and a high level of active factor VIII protein in the blood.

We have thus developed a formulation which makes it possible to administer factor VIII subcutaneously, intramuscularly or intradermally and which gives a great advantage for all patients in need of factor VIII.

Recombinant factor VIII SQ is indicated for treatment of classical haemophilia. The half-life for r-VIII SQ is approximately 12 hours for humans when injected intravenously. For prophylactic treatment 15–25 IU/kg bodyweigt is given of factor VIII three times a week. An intravenous injection is normally 5–10 ml. An injection given subcutaneously is between 0.05 to 1 ml and the concentration of factor VIII must therefore be very high in such a formulation. This is possible to obtain e.g. with our highly purified recombinant factor VIII.

The inventive idea is thus a combination of the finding that factor VIII can be absorbed into the blood-stream when given as a subcutaneous, intramuscular or intradermal pharmaceutical formulation and that it is possible to produce a formulation comprising the required high concentration of factor VIII for this purpose.

The present invention relates to a pharmaceutical formulation for subcutaneous, intramuscular or intradermal administration comprising highly purified recombinant coagulation factor VIII in a concentration of at least 1000 IU/ml, which formulation gives a therapeutic level of factor VIII activity in the blood after administration.

The composition is preferably given subcutaneously. The factor VIII activity in the formulation is at least 1000 IU/ml, preferably more than 1500 IU/ml and most preferably from 5000 to 100 000 IU/ml. The volume given is suitably 0.1 to 2 ml, preferably 0.25 to 1.5 ml, and more preferably 0.5 to 1 ml. The volume can also be 0.1 to 1 ml. Factor VIII is recombinant and it can be either in its full-length form or preferably a deletion derivative thereof. More preferably the deletion derivative is recombinant factor VIII SQ (r-VIII SQ). By deletion derivative is here meant coagulation factor VIII, in which the whole or part of the B-domain is missing. Additionally, the r-VIII SQ molecule can be chemically modified, e.g. by pegylation, covalently lined carbohydrates or polypeptides, in order to improve the stability of the molecule in vivo.

Our used factor VIII is highly purified, i.e. has a specific activity of more than 5000 IU/mg protein, even more than 12 000 IU/mg and is preferably stabilized without the addition of albumin.

The formulation can also comprise sodium or potassium chloride, preferably in an amount of more than 0.1 M.

Calcium (or other divalent metal ions) is necessary for the maintenance of the association of factor VIII heavy and light chain. It is here added as calcium chloride ($CaCl_2$) but other salts such as calcium gluconate, calcium glubionate or calcium gluceptate can also be used. The composition comprises preferably calcium chloride or calcium gluconate in an amount of more than 0.5 mM.

An amino acid is preferably used to buffer the system and it also protects the protein in the amorphous phase if the formulation is freeze-dried. A suitable buffer could be L-histidine, lysine and/or arginine. L-Histidine has primarily been chosen because of the good buffer capacity of L-histidine around pH 7.

The formulation could comprise i) at least 1500 IU/ml of a deletion derivative of recombinant factor VIII ii) at least 0.01 mg/ml of a polyoxyethylene sorbitan fatty acid ester iii) sodium chloride, preferably in an amount of more than 0.1 M.

iv) calcium salt, such as calcium chloride or calcium gluconate, preferably in an amount of more than 0.5 mM.

v) an amino acid such as L-histidine in an amount of more than 1 mM.

A non-ionic surfactant can also be present in the formulation and is then preferably chosen from block co-polymers, such as a poloxamer or polyoxyethylene sorbitan fatty acid ester, such as polyoxyethylene-(20)-sorbitan monolaurate or polyoxyethylene-(20)-sorbitan monooleate. The non-ionic surfactant, if used, should preferably be present in an amount above the critical micelle concentration (CMC). See Wan and Lee, Journal of Pharm Sci, 63, p.136, 1974. The polyoxyethylene sorbitan fatty acid ester is preferably used in an amount of at least 0.01 mg/ml.

To this formulation mono- or disaccharides or sugar alcohols, preferably sucrose, could be added. Also antioxidants such as gluthatione, acetylcystein, tocopherol, methionin, EDTA, citric acid, butyl hydroxy toluene and/or butyl hydroxy anisole could be added. Furthermore, preservatives such as benzyl alcohol, phenol, sorbic acid, parabens and chlorocresol could be added.

The formulation comprises preferably L-histidine and sucrose. The ratio of sodium chloride to L-histidine and sucrose in the composition for freeze-drying is suitably more than 1:1 (w:w), preferably more than 2:1 (w:w).

The formulation could be in a dried form, preferably freeze-dried. The dried product is reconstituted with sterile water for injection or a pharmaceutically acceptable buffer solution, or mixed or reconstituted with an aqueous solution containing absorption enhancers or protease inhibitors before administration.

The claimed formulation can also be a stable aqueous solution ready for administration. It can also be a dispersion, e.g. a suspension, a liposomal formulation or an emulsion.

The formulation could be stored in an oxygen-reduced environment as disclosed in the copending patent application PCT/SE94/00265.

Absorption enhancers or protease inhibitors could be added. Examples of suitable absorption enhancers are phospholipids, fatty acids, bile salts, salicylates and EDTA. Examples of suitable protease inhibitors are aprotinin and EDTA.

The claimed formulation can be prepared by mixing factor VIII with a non-ionic surfactant in an aqueous solution, preferably together with an amino acid such as L-histidine, sodium salt, sucrose and a calcium salt or by eluating factor VIII from the last purification step with a buffer containing a non-ionic surfactant in an aqueous solution, preferably together with sodium salt, sucrose, calcium salt and an amino acid such as L-histidine.

The invention also relates to the use of the claimed formulation for the manufacture of a medicament for subcutaneous, intramuscular or intradermal administration for treating haemophilia, preferably for the use of a deletion derivative of recombinant factor VIII for the manufacture of a medicament for subcutaneous administration. The medicament can be in a stable aqueous solution or dispersion, or freeze-dried. It also relates to a method for treatment of haemophilia by subcutaneous, intramuscular or intradermal administration of the claimed formulation.

The data presented in the examples indicate that r-VIII SQ can be injected subcutaneously and recovered in an active form intravenously in vivo. This is a very surprising finding, as no such formulation have been known earlier.

The protection is not limited to a composition under these examples.

EXPERIMENTAL

Material and Methods

The production of recombinant factor VIII SQ(r-VIII SQ) was essentially performed as described in patent WO-A-91/09122, example 1–3. A DHFR deficient CHO celline (DG44N.Y.) was electroporated with an expression vector containing the r-VIII SQ gene and an expression vector containing the dihydroflolate-reductase gene. Following selection on selective media surviving colonies were amplified through growth in stepwise increasing amounts of methotrexate. Supernatant from the resulting colonies were individually screened for factor VIII activity. A production clone was chosen and this was subsequently adapted to serum free suspension growth in a defined medium and finally a large scale fermentation process was developed. Supernatant is collected after certain time periods and further purified as described below.

The clarified conditioned medium was pH adjusted and applied to a S-Sepharose FF column. After washing, factor VIII was eluated with a salt buffer containing 5 mM $CaCl_2$.

Immunoadsorption was carried out on an immunoaffinity resin where the ligand was a monoclonal antibody (8A4) directed towards the heavy chain of factor VIII. Before loading to the column the S-eluate was treated with 0.3% TNBP and 1% Octoxynol 9.

The column was equilibrated, washed and factor VIII was eluated with a buffer containing 0.05 M $CaCl_2$ and 50% ethylene glycol.

The mAb-eluate was loaded on a Q-Sepharose FF column, equilibrated with the elution buffer in the immunoaffinity step. After washing, factor VIII was eluated with 0.05 M L-Histidine, 0.6 M sodium chloride, 4 mM calcium chloride and pH 6.8.

The Q-eluate was applied to a gel filtration column (Superdex 200 p.g.). Equilibration and elution was carried out with a buffer containing L-histidine, sodium chloride and calcium chloride. The protein peak was collected and the solution was formulated before freeze-drying.

This material of r-VIII SQ was received from the final purification step. The factor VIII activity and the concentration of the inactive components were adjusted by diluting with an appropriate buffer containing polyethylene glycol (PEG). The solution was then sterile filtered (0.22 μm), dispensed and freeze-dried.

EXAMPLE 1

Recombinant factor VIII was prepared according to the method described under Experimental.

The freeze-dried composition containing r-VIII SQ was the following per vial, which was reconstituted in 4 ml sterile water for injection:

| Composition per vial: | |
|---|---|
| L-Histidine, mg | 31.0 |
| Sodium chloride, mg | 70.1 |
| Calcium chloride.(2H$_2$O), mg | 2.35 |
| Polyethylene glycol (PEG 4000), mg | 4.0 |
| Polyoxyethylene-(20)-sorbitan monooleate (Tween 80 ®), mg | 1 |
| VIII:C charged, IU/vial | 4400 |
| VIII:C in reconstituted solution, IU/ml | 1060 |

Male albino mice weighing about 30 g and of strain NMRI, SPF, were injected subcutaneously in the neck with the reconstituted r-VIII Sq solution. The volume injected at the dose level of 10 000 IU/kg was 9.4 ml/kg and at the higher dose level 50 000 IU/kg, 5 times larger, 47 ml/kg. In the placebo treatment saline was used, 9.4 ml/kg. 3–5 minutes before the blood sampling the mice were anaesthetized intra peritoneally with Mebumal® (pentobarbital) vet. 60 mg/ml. The volume injected was 9.4 ml/kg i.e. about 0.3 ml/mouse. Under the anaesthesia 0.45 ml blood was collected from the vena cava in plastic syringes containing 0.05 ml 0.13 M sodium citrate. Plasma was then prepared from the collected blood by centrifugation (8800 g for 7 minutes) and kept frozen in plastic Cryoflex tubes at −70° C. until the time of determination of factor VIII activity.

Results:

TABLE 1

VIII:C in plasma from mice receiving r-VIII SQ 10000 IU/kg body weight subcutaneously.

| Time after administration (hours) | VIII:C (IU/ml) X ± Sd | n number of observations |
|---|---|---|
| 0 | 0.82 ± 0.43 | 12 |
| 0.33 | 1.23 ± 0.41 | 3 |
| 1.0 | 1.38 ± 0.56 | 4 |
| 1.5 | 1.83 ± 0.60 | 12 |
| 2.0 | 1.43 ± 0.91 | 8 |
| 4.0 | 1.34 ± 0.72 | 6 |
| 6.0 | 1.27 ± 0.42 | 4 |

TABLE 1-continued

VIII:C in plasma from mice receiving r-VIII SQ 10000 IU/kg body weight subcutaneously.

| Time after administration (hours) | VIII:C (IU/ml) X ± Sd | n number of observations |
|---|---|---|
| 8.0 | 1.55 ± 0.80 | 4 |
| 16.0 | 0.62 ± 0.28 | 4 |
| 20.0 | 0.58 ± 0.12 | 3 |
| 24.0 | 0.76 ± 0.53 | 4 |

TABLE 2

Dose - Response in mice receiving r-VIII SQ subcutaneosly.
Dose: Dose r-VIII SQ administrated (IU/kg).
Response: VIII:C in plasma (IU/ml) 1.5 hours after subcutaneous administration.

| Dose (IU/kg) | Response (IU/ml) | Response (IU/ml) (baseline adjusted) | n number of obs. |
|---|---|---|---|
| Blank (baseline) | 0.82 ± 0.43 | — | 12 |
| Saline | 1.21 ± 0.34 | 0.39 | 4 |
| 10000 | 1.83 ± 0.60 | 1.01 | 12 |
| 50000 | 2.47 ± 0.60 | 1.65 | 6 |

Results

1. The change of VIII:C in plasma with time after a subcutaneous dose of r-VIII SQ, 10 000 IU/kg, shows the typical pattern for a drug being absorbed from a subcutaneous depot (see Table 1). The maximum VIII:C level in plasma is seen at about 1.5 hours after administration (see Table 1).

2. The absorption of r-VIII SQ from a subcutaneous depot is further verified by the increase in maximum concentration seen when the dose is increased five-fold. No significant effect was observed on the obtained plasma level of VIII:C when the subcutaneous injection volume was changed from 9.4 to 47 ml/kg while the dose of r-VIII Sq was kept constant. Furthermore, the VIII:C obtained in plasma was essentially not dependent on the osmolality of the administration solution.

3. The bioavailability of r-VIII SQ after subcutaneous administration in mouse was about 10% of the bioavailability after intravenous administration. The bioavailability was calculated from the area under the activity (VIII:C)—time curve.

EXAMPLE 2

Plasma derived factor VIII was used.

The composition of the frozen solution containing plasma derived factor VIII was the following:

| Composition per ml: | |
|---|---|
| L-Histidine, mg | 7.8 |
| Sodium chloride, mg | 35.1 |
| Calcium chloride.(2H$_2$O), mg | 0.59 |
| Polyethylene glycol (PEG 4000), mg | 1.0 |
| Albumin human, mg | 10.0 |
| VIII:C, IU/ml | 250 |

Male albino mice weighing about 30 g and of strain NMRI, SPF, were injected subcutaneously in the neck with the reconstituted factor VIII solution.

The volume injected at the dose level of 10 000 IU/kg was about 40 ml/kg. In the placebo treatment a solution containing 9% (w/v) sodium chloride was used. 3–5 minutes before the blood sampling the mice were anaesthetized intra peritoneally with Mebumal® (pentobarbital) vet. 60 mg/ml. The dose volume was about 1.2 ml/mouse. Under anasthesia 0.45 ml blood was collected from vena cava in plastic syringes containing 0.05 ml sodium citrate (0.13 M). Plasma was prepared from the blood by centrifugation (8800 g for 7 minutes) and thereafter stored in plastic Cryoflex tubes at −70 °C. until determination of VIII:C.

Results:

TABLE 3

VIII:C in plasma from mice receiving plasma derived factor VIII, 10000 IU/kg, subcutaneously. VIII:C in the administration solution was about 250 IU/ml.

| Time after administration (hours) | VIII:C (IU/ml) X ± SD | n number of observations |
|---|---|---|
| 0 | 1.04 ± 0.30 | 4 |
| 1 | 1.20 ± 0.53 | 4 |
| 1.5 | 1.39 ± 0.04 | 4 |
| 2 | 0.85 ± 0.34 | 4 |
| 4 | 1.19 ± 0.49 | 4 |
| 6 | 1.32 ± 0.53 | 4 |
| 8 | 1.15 ± 0.39 | 4 |
| 16 | 1.27 ± 0.08 | 4 |
| 20 | 1.17 ± 0.41 | 4 |
| 24 | 1.32 ± 0.21 | 4 |

Results:

1. The bioavailability of plasma derived factor VIII is fairly low according to the results of the in vivo study in mice (Table 3). The bioavailability of plasma derived factor VIII is roughly about 1/10 of the bioavailability of r-VIII SQ. Hence, the bioavailability of r-VIII SQ is substantially higher than the bioavailability of factor VIII derived from human plasma. The maximum plasma level of VIII:C is seen about 1.5 hours after subcutaneous administration.

EXAMPLE 3

Recombinant factor VIII was prepared according to the method described under Experimental with the following exceptions: (i) the material of r-VIII SQ that was received from the final purification step was diluted with a buffer not containing PEG, (ii) the r-VIII SQ solution was not freeze-dried, it was stored at −70° C.

The r-VIII SQ-solution had the following composition:

| Composition per vial: | |
|---|---|
| L-Histidine, mg | 7.5 |
| Sucrose, mg | 158 |
| Sodium chloride, mg | 45 |
| Calcium chloride.(2H$_2$O), mg | 1.25 |
| Polyoxyethylene-(20)-sorbitan monooleate (Tween 80 ®, mg) | 0.50 |
| VIII:C charged, IU/vial | 6070 |
| VIII:C, IU/ml* | 1130 |

*Diluted r-VIII SQ-solution (1 part of r-VIII SQ-solution + 1 part of water, v:v)

The r-VIII SQ-solution was diluted with sterile water for injection (1 part of r-VIII SQ-solution+1 part of water, v:v) prior to administration when the dose of VIII:C was below 3000 IU/kg body-weight.

Female cynomolgus monkey (*Macaca fascicularis*) weighing about 3–3.5 kg were injected with the r-VIII SQ-solution subcutaneously in the dorsal region. Depending on the dose, the volume of injection was varied between approximately 0.2 to 2.0 ml/kg body-weight. Subcutaneous injections with single doses of 250, 2500 and 5000 IU/kg were administered. On each sampling occasion 1.8 ml of blood was collected into tubes containing citrate as anticoagulant (0.2 ml). After centrifugation plasma was separated and frozen in aliquots (<−60° C.).

Results:

TABLE 4

VIII:C in plasma from monkeys receiving r-VIII SQ, 250 IU/kg, subcutaneously. The VIII:C in the administration solution was about 1130 IU/ml.

| | Monkey No | | |
|---|---|---|---|
| Sampling after inj. (Hours) | 1 VIII:C (IU/ml) | 2 VIII:C (IU/ml) | 3 VIII:C (IU/ml) |
| 0 | 2.15 | 1.49 | 1.76 |
| 1 | 2.32 | 1.75 | 1.92 |
| 4 | 2.43 | 1.52 | 1.89 |
| 8 | 2.48 | 1.67 | 1.92 |
| 10 | 2.41 | 1.76 | 2.03 |
| 12 | 2.29 | 1.70 | 2.01 |
| 14 | 2.20 | 1.69 | 2.00 |
| 24 | 1.76 | 1.32 | 1.98 |
| 30 | 2.31 | 1.46 | 1.90 |
| 48 | 2.18 | 1.64 | 1.96 |

TABLE 5

VIII:C in plasma from monkeys receiving r-VIII SQ, 2500 IU/kg, subcutaneously. The VIII:C in the administration solution was about 1130 IU/ml.

| | Monkey No | | |
|---|---|---|---|
| Sampling after inj. (Hours) | 4 VIII:C (IU/ml) | 5 VIII:C (IU/ml) | 6 VIII:C (IU/ml) |
| 0 | 1.95 | 1.35 | 2.30 |
| 2 | 2.43 | 1.86 | 3.05 |
| 6 | 3.51 | 2.45 | 3.59 |
| 9 | 3.91 | 2.47 | 4.16 |
| 11 | 3.47 | 2.24 | 3.68 |
| 13 | 3.11 | 2.06 | 3.34 |
| 22 | 2.38 | 1.55 | 2.79 |
| 40 | 2.01 | 1.49 | 2.38 |

TABLE 6

VIII:C in plasma from monkeys receiving r-VIII SQ, 5000 IU/kg, subcutaneously. The VIII:C in the administration solution was about 2470 IU/ml.

| | Monkey No | | |
|---|---|---|---|
| Sampling after inj. (Hours) | 7 VIII:C (IU/ml) | 8 VIII:C (IU/ml) | 9 VIII:C (IU/ml) |
| 0 | 2.04 | 1.78 | 1.54 |
| 2 | 2.99 | 2.37 | 2.99 |
| 6 | 4.56 | 3.33 | 5.32 |
| 9 | 4.75 | 3.89 | 5.70 |
| 11 | 4.72 | 3.82 | 5.46 |
| 13 | 4.23 | 3.06 | 4.63 |
| 22 | 3.03 | 2.33 | 3.46 |
| 40 | 2.76 | 1.77 | 2.60 |

TABLE 7

Dose - Response in monkey receiving r-VIII SQ subcutaneously.
Dose: Dose r-VIII SQ administrated (IU/kg bodyweight).
Response: VIII:C in plasma (IU/ml) about 9 hours after administration.

| Dose (IU/kg) | Response (IU/ml) | Response (IU/ml, baseline adj.) | n number of observations |
|---|---|---|---|
| Blank (baseline) | 1.8 ± 0.3 | — | 9 |
| 250 | | 0.37 ± 0.05 | 3 |
| 2500 | | 1.70 ± 0.06 | 3 |
| 2500 | | 2.05 ± 0.57 | 3 |
| 5000 | | 3.4 ± 1.20 | 3 |

Results

1. According to the results (table 4–6) the plasma concentration as a function of time follows the typical pattern for a drug being absorbed. after subcutaneous administration. The maximum concentration of VIII:C is seen about 9 hours after administration.

2. The dose-response relationship obtained (table 7), gives a further verification that there is an absorption of VIII:C into the blood stream following a subcutaneous injection.

3. The bioavailability of r-VIII Sq after subcutaneous administration in monkey was about 5–10%. The bioavailability was calculated from the area under the activity (VIII:C)—time curve. The bioavailability was essentially independent of the dose of r-VIII SQ,

What is claimed is:

1. Method for treatment of haemophilia by subcutaneous, intramuscular or intradermal administration of pharmaceutical formulation with a volume of 0.1 to 2 ml comprising a highly purified recombinant coagulation factor VIII with an activity of at least 1,000 IU/ml and a non-ionic surfactant, wherein said recombinant coagulation factor VIII is selected from the group consisting of deletion derivatives of factor VIII where the whole or part of the B-domain is missing and factor VIII which has been chemically modified by pegylation or covalently linked carbohydrates or polypeptides, which formulation is stabilized without albumin and is capable of increasing the factor VIII activity in the blood to a therapeutic level after subcutaneous, intramuscular or intradermal administration.

2. A method according to claim 1 in which the factor VIII activity is from 5000 to 100000 IU/ml.

3. A method according to claim 1 wherein the formulation has a volume of 0.5 to 1 ml.

4. A method according to claim 1 wherein said deletion derivative of recombinant coagulation factor VIII has a molecular weight of 170 kDa to 300 kDa.

5. A method according to claim 1 wherein said recombinant coagulation factor VIII is a deletion derivative of factor VIII where the whole or part of the B-domain is missing.

6. A method according to claim 1 wherein said recombinant coagulation factor VIII is factor VIII which has been chemically modified by pegylation or covalently linked carbohydrates or polypeptides.

7. A method according to claim 1 which comprises subcutaneous administration.

8. A method according to claim 7 wherein the formulation has a volume of 0.1 to 2 ml.

9. A method according to claim 7 in which the factor VIII activity is from 5000 to 100000 IU/ml.

10. A method according to claim 1 in which the factor VIII activity is more than 1500 IU/ml.

11. A method according to claim 10 wherein the formulation has a volume of 0.1 to 2 ml.

12. A method according to claim 1 in which the deletion derivative factor VIII is deletion derivative recombinant factor VIII SQ(r-VIII SQ).

13. A method according to claim 1 wherein the formulation is a stable aqueous solution ready for administration.

14. A method according to claim 1 wherein the formulation is freeze-dried and reconstituted with sterile water or a pharmaceutically acceptable buffer solution before administration.

15. A method according to claim 1 wherein the formulation is mixed or reconstituted with an aqueous solution containing absorption enhancers or protease inhibitors before administration.

16. Method for treatment of haemophilia by subcutaneous, intramuscular or intradermal administration of pharmaceutical formulation with a volume of 0.1 to 2 ml, comprising a highly purified recombinant coagulation factor VIII with an activity of at least 1500 IU/ml and a non-ionic surfactant, wherein said recombinant coagulation factor VIII comprises a deletion derivative of factor VIII where the whole or part of the B-domain is missing; said non-ionic surfactant comprises at least 0.01 mg/ml of a polyoxyethylene sorbitan fatty acid ester; and the formulation further comprises sodium chloride, calcium salt and an amino acid in an amount of more than 1 mM; which formulation is stabilized without albumin and is capable of increasing the factor VIII activity in the blood to a therapeutic level after subcutaneous, intramuscular or intradermal administration.

17. The method according to claim 16 wherein said sodium chloride is present in an amount of more than 0.1 M, said calcium salt is calcium chloride or calcium gluconate and is present in an amount of more than 0.5 mM, and wherein said amino acid is L-histidine.

18. A method according to claim 16 in which the deletion derivative factor VIII is deletion derivative recombinant factor VIII SQ (r-VIII SQ).

* * * * *